United States Patent [19]

Jurd

[11] 3,959,489

[45] May 25, 1976

[54] POLYBUTYL-2-CINNAMYLPHENOLS AS INSECT ANTI-PROCREANTS

[75] Inventor: Leonard Jurd, Berkeley, Calif.

[73] Assignee: The United States of America as represented by the Secretary of Agriculture, Washington, D.C.

[22] Filed: Mar. 24, 1975

[21] Appl. No.: 561,583

[52] U.S. Cl. .............................. 424/346; 260/624 B
[51] Int. Cl.² ............................................ A01N 9/26
[58] Field of Search .......... 424/346; 260/619, 624 B

[56] References Cited
UNITED STATES PATENTS

| | | | |
|---|---|---|---|
| 3,635,885 | 1/1972 | Starnes | 260/624 B |
| 3,745,222 | 7/1973 | Jord, et al. | 424/346 |
| 3,839,586 | 10/1974 | Ludrik | 424/337 |

OTHER PUBLICATIONS

Annual Review of Biochemistry, Vol. 40, pp. 781, 1096 & 1097 (1971).

*Primary Examiner*—Leonard Schenkman
*Attorney, Agent, or Firm*—M. Howard Silverstein; Max D. Hensley; William Takacs

[57] ABSTRACT

New polybutyl-2-cinnamylphenols, particularly 4,6-di-t-butyl-2-cinnamylphenol, are useful for insect control and especially as insect chemosterilants and oviposition inhibitors.

8 Claims, No Drawings

POLYBUTYL-2-CINNAMYLPHENOLS AS INSECT ANTI-PROCREANTS

DESCRIPTION OF THE INVENTION

This invention relates to and has among its objects the provision of novel organic compounds, namely, polybutyl-2-cinnamylphenols, and the use thereof in insect control, particularly as anti-procreants. Further objects of the invention will be evident from the following description wherein parts and percentages are by weight unless otherwise specified.

The abbreviation ppm used herein refers to parts per million. The symbol $\phi$ is used herein to represent the phenyl

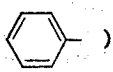

group.

One aspect of the invention concerns the provision of new organic compounds, namely, polybutyl-2-cinnamylphenols. These compounds have the structure

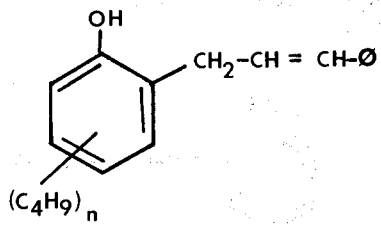

wherein $n$ is 2 or 3.

The compounds of the invention may be prepared by refluxing a mixture of the appropriate polybutylphenol and cinnamyl alcohol in aqueous formic acid. For example, the preferred compound of the invention (4,6-di-t-butyl-2-cinnamylphenol) can be prepared by reacting 2,4-di-t-butylphenol with cinnamyl alcohol under reflux in the presence of aqueous formic acid. This synthesis is illustrated by the following formulas

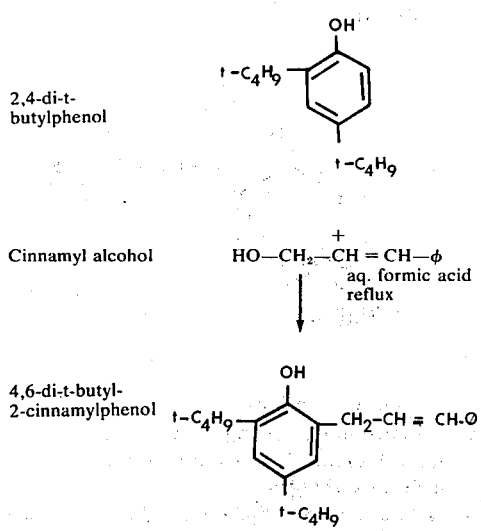

USE OF THE NEW COMPOUNDS

Effective means of biologically controlling insect populations encompasses two distinct concepts. First, a chemical may be administered to the insects, which then become sexually sterile. The sexually sterilized insects mate with fertile insects, but the eggs laid do not yield any progeny. The result is a decrease in population of the insects. Another method of biological control involves administering a chemical to the insects, with the result that the female species do not posit (lay) any eggs. Consequently, no progeny are produced and a decrease in insect population is thus attained. Although the above means of biological control encompass two distinct ideas, the chemical compounds which produce the above effects may be termed generally as anti-procreants, that is, compounds which act either as chemosterilants or as oviposition inhibitors and prevent procreation of the species.

The biological method of insect control offers many advantages over the usual method of applying an insecticide to insects or their habitat. For example, it avoids harm to humans, animals, and useful insects (bees, for instance).

In controlling insects by sterilization or oviposition inhibition, a suitable compound is administered to a group of insects and these are then released in a locus where insects of the same species are present. As noted above, the treated insects mate with fertile ones but without producing progeny so that the overall population is decreased.

It has been found that the compounds of the invention are useful as anti-procreants and thus can be used in the above-mentioned methods of biological insect control. Thus, in a practice of this phase of the invention, insects are rendered either sexually sterile or, in the case of female insects, incapable of oviposition by administering to them any of the compounds heretofore described. The so-treated insects are then ready for release in insect breeding areas for mating with fertile insects of the same species. The administration of the compounds may be carried out by feeding the insects on a conventional insect food to which is added any of the aforesaid compounds in a concentration which is sufficient to induce either sexual sterility or oviposition inhibition in the insects, but is insufficient to kill them. The concentration required to achieve sterility or oviposition inhibition will vary depending on such factors as the kind of insect and the activity of the selected anti-procreant. It should be noted that the compounds of the invention are capable of acting as either a chemosterilant or an oviposition inhibitor depending on the particular concentration administered to the insects. In any particular case the appropriate amount to use can readily be determined by pilot tests well-known to entomologists. The anit-procreants of the invention can be administered to captive insects in cages or other suitable containers. Alternatively, the anit-procreants may be administered to wild insects, for example, by making available to them feeding stations provided with insect food admixed with any of the anit-procreants in either a sterilizing or an oviposition inhibiting proportion.

EXAMPLES

The invention is further demonstrated by the following illustrative examples.

EXAMPLE 1

Preparation of 4,6-Di-t-butyl-2-cinnamylphenol (DBCP)

A mixture of 2,4-di-t-butylphenol (206 g.) and cinnamyl alcohol (134 g.) in 88% formic acid (600 ml.)

| Compound used | Amount of compound in food (%) | Mortality, parent generation (%) | Oviposition | Egg hatch (%) | Pupal development (%) |
| --- | --- | --- | --- | --- | --- |
| DBCP | 1.00 | 0 | None | 0 | 0 |
| do. | 0.50 | 0 | None | 0 | 0 |
| do. | 0.25 | 0 | Normal | 0 | 0 |
| do. | 0.10 | 0 | Normal | 21 | 21 |
| None | 0 | 0 | Normal | 92–93 | 92–93 | was refluxed for 1.5 hours. Warm water (1 liter) was added to the mixture and the oily layer which formed at the top was collected. This material was distilled and the fraction boiling between 200°–202° C. at 0.05 mm. of Hg was collected (143 g.). On cooling, this material crystallized and the solid was recrystallized from methanol to give colorless prisms, m.p. 89° C. The nuclear magnetic resonance (nmr) spectrum of DBCP at 100 MHz in deuterated chloroform ($CDCl_3$) exhibited absorbances as follows: a singlet (9 protons) at $\delta$ 1.31, a singlet (9 protons) at $\delta$ 1.42, a doublet (2 protons) at $\delta$ 3.55 (coupling constant = J = 6.0 Hz), a singlet (1 proton) at $\delta$ 5.09, a multiplet (2 protons) at $\delta$ 6.20–6.67, a doublet (1 proton) at $\delta$ 7.03 (J = 3.0 Hz), and a multiplet (6 protons) at $\delta$ 7.13–7.37.

EXAMPLE 2

Anti-procreant Tests

These experiments concern testing of DBCP prepared in Example 1 for inducing sterility or inhibiting oviposition in house flies (*Musca domestica*).

DBCP was administered in a standard fly food containing 6 parts of sugar, 6 parts of powdered non-fat dry milk, and 1 part of powdered egg yolk. Treated food was prepared by mixing an appropriate amount of a solution or suspension of CBCP in acetone with a batch of the food. The acetone was evaporated (4–6 hours) and the dry material was repulverized.

Oviposition Inhibition Tests

Samples of treated food with a container of water were placed in cages containing 100 newly-emerged adult flies. After the flies had been exposed to the treated diet for 6–7 days, ½ inch of moist standard fly larva-rearing medium (CSMA) in souffle cups was placed in the cages for oviposition. After 4–6 hours, the cup was removed and examined for eggs. If no eggs were laid, the medium was offered again at intervals of 1 to 2 days until it had been offered three times or the flies had oviposited.

Chemosterilancy Tests

If eggs were laid in the above tests, the cups were filled with water and stirred to break up the egg masses. A random sample of 100 eggs from each cup was collected and placed on a small piece of black cloth which was then laid on top of moist larva-rearing medium in a rearing container. Observations were made to determine percentage of egg hatch and pupal development.

In those cases where the preliminary tests indicated that sterility had occurred in the flies fed the treated food, 10 males were removed from the test cage and crossed with 10 virgin, 4-day old, untreated females. These flies were maintained on untreated fly food. After 5 days, cups containing the larval-rearing medium was provided as previously described and a 100-egg sample was collected and placed on moist larva-rearing medium. About a week after oviposition, examination was made to determine the percentage of hatched eggs and of pupae developed.

The results of the oviposition inhibition tests and the chemosterilancy tests are summarized below:

For purpose of comparison the above-described tests were applied to 4-cinnamylphenol, 2-methyl-4-cinnamylphenol, 2,6-dimethyl-4-cinnamylphenol, 4-ethyl-2-cinnamylphenol, 4-t-butyl-2-cinnamylphenol, 4-methoxy-2-cinnamylphenol, 4-nonyl-2-cinnamylphenol, 4-octyl-2-cinnamylphenol, 4-(2-phenyl-2-propyl)-2-cinnamylphenol, 2-i-propyl-5-methyl-4-cinnamylphenol, 4-methyl-6-t-butyl-2-cinnamylphenol, 2-phenyl-4-cinnamylphenol, 2,6-di-t-butyl-4-cinnamylphenol, and 4-t-pentyl-2-cinnamylphenol. The tests demonstrated that these compounds were ineffective in inducing sexual sterility or in inhibiting oviposition.

Having thus described the invention, what is claimed is:

1. A method of inhibiting oviposition in flies, which comprises
   providing for ingestion by the flies a compound of the structure

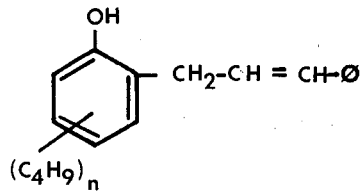

wherein $n$ is 2 or 3,
said compound being provided in an amount insufficient to kill the flies but sufficient to inhibit oviposition therein.

2. The method of claim 1 wherein the compound is 4,6-di-t-butyl-2-cinnamylphenol.

3. A method of causing sexual sterility in flies, which comprises
   providing for ingestion by the flies a compound of the structure

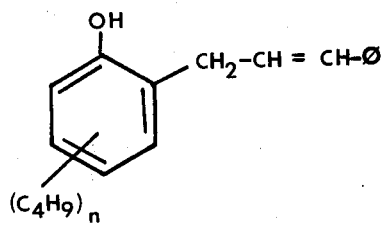

wherein $n$ is 2 or 3,
said compound being provided in an amount insufficient to kill the flies but sufficient to induce sexual sterility therein.

4. The method of claim 3 wherein the compound is 4,6-di-t-butyl-2-cinnamylphenol.

5. A composition for inhibiting oviposition in flies, consisting essentially of
   a. a fly food, and
   b. a compound of the structure

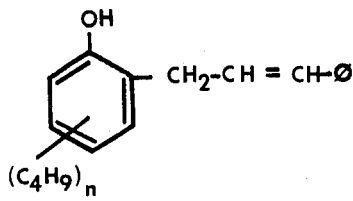

wherein *n* is 2 or 3, in an amount insufficient to kill flies which ingest the composition but sufficient to inhibit oviposition therein.

6. The composition of claim 5 wherein the compound is 4,6-di-t-butyl-2-cinnamylphenol.

7. A composition for inducing sexual sterility in flies, consisting essentially of a. a fly food, and
b. a compound of the structure

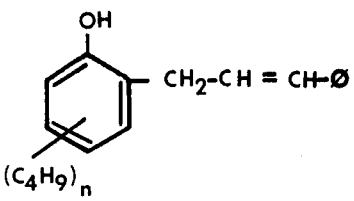

wherein *n* is 2 or 3, in an amount insufficient to kill flies which ingest the composition but sufficient to induce sexual sterility therein.

8. The composition of claim 7 wherein the compound is 4,6-di-t-butyl-2-cinnamylphenol.

* * * * *